United States Patent [19]

Chornenky et al.

[11] Patent Number: 5,582,171
[45] Date of Patent: Dec. 10, 1996

[54] APPARATUS FOR DOPPLER INTERFEROMETRIC IMAGING AND IMAGING GUIDEWIRE

[75] Inventors: Victor Chornenky, Minnetonka; Peter Fettig, St. Louis Park, both of Minn.

[73] Assignee: Insight Medical Systems, Inc., Minnetonka, Minn.

[21] Appl. No.: 272,764

[22] Filed: Jul. 8, 1994

[51] Int. Cl.$^6$ ........................................ A61B 6/00
[52] U.S. Cl. .................... 128/653.1; 128/664; 128/666
[58] Field of Search ................ 128/653.1, 633–634, 128/664–666, 656–658, 772; 604/96, 97; 356/345

[56] References Cited

U.S. PATENT DOCUMENTS

| | | | |
|---|---|---|---|
| 4,587,972 | 5/1986 | Morantte, Jr. | 128/660 |
| 4,718,417 | 1/1988 | Kittrell et al. | 128/303 |
| 4,887,605 | 12/1989 | Angelsen et al. | 128/660 |
| 5,009,655 | 4/1991 | Daignault, Jr. et al. | 606/7 |
| 5,029,588 | 7/1991 | Yock et al. | 128/662 |
| 5,095,911 | 3/1992 | Pomeranz | 128/662 |
| 5,104,392 | 4/1992 | Kittrell et al. | 606/15 |
| 5,106,387 | 4/1992 | Kittrell et al. | 606/15 |
| 5,109,859 | 5/1992 | Jenkins | 128/662 |
| 5,217,456 | 6/1993 | Narciso, Jr. | 606/15 |

FOREIGN PATENT DOCUMENTS

WO9219930 11/1992 WIPO.
WO9412095 11/1993 WIPO.

*Primary Examiner*—Ruth S. Smith
*Attorney, Agent, or Firm*—Janal M. Kalis; Jennifer K. Farrar

[57] ABSTRACT

An apparatus for Doppler interferometric imaging comprising a balanced fiber optic interferometer, a low coherence light source and an imaging guidewire is used for diagnosis of intravascular obstructions. The imaging guidewire, which is also used for placement of over-the-wire catheters, comprises a hollow elongated body, an optical fiber, a rotatable mirror at its distal end and a micromotor operable to sweep the sampling beam around the vessel. An optical length modulator in the reference arm of the interferometer provides ramp wise modulation of optical length and a Doppler frequency shift for the reference beam. The polarization diversity detection scheme and two envelope detectors tuned for the Doppler frequency, perform measurements of the intensities of the two linear polarizations of the retroreflected light. Combined with current values of the optical length of the reference arm and angular position of the sweeping mirror, this information is used for reconstruction of the cross-sectional images of the vessel in two polarizations. These images are used for measurements of the geometry and recognition of the morphology of an intravascular obstruction which is utilized for diagnosis of atherosclerosis and real-time guidance of interventional procedures like PTCA.

12 Claims, 7 Drawing Sheets

APPARATUS FOR DOPPLER INTERFEROMETRIC IMAGING AND IMAGING GUIDEWIRE

BACKGROUND OF THE INVENTION

The present invention relates generally to the construction and use of intravascular catheters and, more specifically, to catheters which may be used both as a guidewire for positioning over-the-wire catheters and as a Doppler interferometric imaging catheter for intravascular diagnosis of atherosclerosis.

Atherosclerosis is a common human disease characterized by the deposition of fatty substances (atherosis) in, and a fibrosis of the inner layer of the arteries (sclerosis). Accumulated in blood vessels, these depositions restrict the blood flow and place a person's health at serious risk.

Multiple interventional therapeutic techniques have been developed recently for reduction or elimination of obstructing plaque and restoration of the patency of the vessel. Among these techniques are: balloon dilation, tip abrasion, atherectomy, laser ablation, placing stents and thrombolytic therapy.

Atherosclerotic lesions can be of different geometries, degree of progression, and/or complicated with calcification and thrombi. None of the mentioned techniques is universal, each of them has it's own situational advantages and contraindications, so different types of atherosclerotic lesions require different therapeutic interventions. To make an educated choice of an appropriate therapeutic modality and specify the dimensions of the therapeutic tooling, such as diameter, length, etc., it is necessary to have complete diagnostic information about the lesion, which includes its geometry and composition. But present imaging technology severely limits the ability of cardiologists to get this information prior to intervention and to guide intervention in real time.

There is a strong unsatisfied demand for an advanced imaging system capable of providing adequate information in diagnostic support and guidance of intravascular intervention, especially in the most widely used interventional technique: Percutaneous Transluminal Coronary Angioplasty (PTCA).

The most commonly employed modality for vascular imaging is angiography. It provides two dimensional blood flow mapping. A radiopaque dye is injected into the vessels being visualized and X-ray fluoroscopy indicates the path of the dye flow as a dark projection path on a white background. It enables an interventionalist to find the location of the stenotic area and assists in inserting guidewires and catheters into the diseased vessel for performing PTCA. Angiography shows the boundaries between the blood and inner surface of the vessel and has very limited ability to provide information about composition of intravascular obstructions and their geometry. Angiography is also used for examining the final patency of the vessel, and overall assessment of the outcome of the PTCA procedures.

Angioscopy supplies visual information on the luminal surface. To function, angioscopy requires flushing the blood from the vessel and replacing it with optically transparent saline. This special procedure requires temporarily occluding the vessel, stopping the blood supply to the heart and can cause prolonged ischemia. Because of this drawback, angioscopy is used very rarely, mainly for research purposes.

Laser induced fluorescence (LIF) employed for differentiation of diseased and healthy tissue so far has had very limited success. It does not provide geometric information about the diseased vessel and it's ability to guide a therapeutic procedure is questionable. Similarly, this is true of many of the newer proposed spectroscopies, such as Raman, or Plasma emission.

The intravascular ultrasound imaging technique (IVUS) has been developed in the past several years. In this approach an ultrasound emitter and a receiver are placed inside an artery and are supplied with a means to rotate the beam around the vessel.

Reflected ultrasound energy from the surface of the lumen and it's subintimal structures is collected by the receiver and processed by a computer. A cross-sectional reflectance image is thus generated and displayed on a video monitor. The architecture of the vessel, atherosclerotic plaque and calcification can be observed. But as recent studies have demonstrated, IVUS lacks several crucial features: 1) It does not provide some very important information, for example, discerning thrombus from soft atheroma (fatty lesion); 2) IVUS catheters are big and cannot be used simultaneously with a therapeutic catheter inside the artery—for diagnosis and evaluation of the results of the intervention it takes additional procedures to insert them into the artery and pull them back before and after the therapeutic procedure; and 3) They are relatively expensive. To meet hospital requirements for standard equipment of that kind, they should be significantly cheaper.

A known imaging catheter is described in Pomeranz U.S. Pat. No. 5,095,911. The device employs an ultrasound transducer and rotating mirror to scan the interior of a vessel. A drive cable which is driven from outside the patient causes the transducer and the reflective surface to rotate as a unit. The catheter body is formed of a flexible wire coil coated with a polymeric material. The catheter body is flexible enough to manipulate within the patient's vascular system, but has torsional stiffness sufficient to allow for rotation to position and guide the catheter through the vascular system. The outer diameter of the catheter body, according to the author, and the end containing the ultrasound transducer is between about 0.3 and 1 millimeter. However, there are currently no known ultrasound transducers having outer diameters which are smaller than 0.8 millimeters.

Projecting from an end of the housing containing the ultrasound transducer, opposite the end connected to the catheter body is a fixed guidewire with a deviated tip.

The guidewire portion is used to position the ultrasound transducer probe for imaging. The probe as well as the catheter body are much larger in diameter than the diameter of the guidewire. The diameter is too large to use in connection with most over-the-wire therapeutic catheters, in particular, catheters used in PTCA procedures, which require an 0.35 millimeter or smaller outer diameter guidewire. In addition, the therapeutic catheter should be moved away from the lesion and the probe must be moved back and forth across the diseased tissue to form an image between interventional actions.

Angelsen et al. U.S. Pat. No. 4,887,605 describes a laser catheter which includes ultrasound imaging capability. At the distal end of the catheter is a housing which contains an ultrasound transducer for emitting an ultrasonic beam. A cylindrical housing is provided having a central throughbore. An optical fiber is positioned in the throughbore and is used to deliver a beam from a laser to the tissue to be treated. The catheter described in this patent is intended to be used as a diagnostic and therapeutic catheter, and is not intended to function as an imaging guidewire. Furthermore, by combining the diagnostic means with the therapeutic means, the user has sacrificed the ability to choose the most appropriate therapeutic treatment for a given situation. The combination of these two means would imply that the choice of therapy is made without prior knowledge of the geometry and morphology of the diseased vessel.

Another known ultrasound imaging and laser catheter is described in Morantte, Jr. U.S. Pat. No. 4,587,972. This catheter includes a bundle of optical fibers extending through a cylindrical body for delivering a laser beam. The device also includes an ultrasound transducer at its distal end for imaging vascular obstructions. The distal end contains a number of electrodes which generate ultrasonic waves when energized that travel axially of the cylindrical body, providing a scanning angle of 30–45 degrees. This device has the same drawbacks as the device described in U.S. Pat. No. 4,887,605.

Using current technology, it is not possible to reduce the size of an ultrasound probe small enough to pass through a central cavity of a therapeutic catheter, such as a balloon catheter. In order to incorporate such a probe into a distal end of a guidewire, a housing of the ultrasound probe would need to have a maximum outer diameter of 0.35 millimeters. Such guidewires and some which are up to about 0.46 millimeters at the most, are currently in wide use in procedures such as PTCA.

The use of ultrasound imaging and angiography for geometric measurement have some distinct problems. The radiopaque dye used to identify the vessel boundaries penetrates diffused atherosclerotic lesions, causing the inner diameter of the diseased region of the vessel to appear larger than it actually is. Similarly, the sound waves emanating from an ultrasound transducer are not all reflected from the obstruction, creating an image with a blurred outline of the inner diameter of the vessel. The uncertainty in the measurement of a diameter of the blood vessel using either technique can be as high as 0.5 millimeters. Studies have shown that measurements taken on the same lesion from angiography and ultrasound do not correlate. The error is so large that the appropriate size therapeutic balloon catheter cannot be accurately determined.

Other imaging devices are known which are used as over-the-wire catheters. One such device is shown in Narciso, Jr. U.S. Pat. No. 5,217,456. An intravascular optical radial imaging system is described which utilizes the spectral qualities of tissue to identify the composition of the vessel. The main disadvantage of this device is that it requires removal prior to treating the vessel, and therefore the device is incapable of imaging during therapeutic treatment. The device also does not provide any geometric information about the vessel.

The use of low coherence interferometry for imaging biological tissue is generally known. PCT international publication WO 92/19930 describes a device which includes a low coherence light source that supplies light to two optical paths. The first path is for sampling and sends light to a probe. The second path is phase modulated and functions as a reference arm. The second optical path includes a mirror that traverses back and forth along a longitudinal path. The return reflective energy is combined and the output is converted into an electrical signal. The electrical signal is inputted into a computer which uses the information to create a visual image of the object being scanned.

Although this configuration provides optical imaging using interferometry, the amount of time needed for taking an image is too long for intravascular use. In order for intravascular imaging to be of maximum use during a procedure, the scanning process must take place within a fraction of a beat of the patient's heart. In addition, the device disclosed in international publication WO 92/19930 is incapable of being scaled down small enough to be utilized in an imaging guidewire that is compatible with PTCA instrumentation. The imaging device described in this reference is about 2 millimeters in diameter as compared to a guidewire outer diameter of 0.35 millimeters.

In P.C.T. international publication WO 9412095, a new imaging modality based on Low Coherence Interferometry is described. This approach to diagnostic imaging came into biology from the telecommunications industry, where it was employed for quality control of optical elements and fibers. In this approach light, instead of ultrasound, is used for diagnosis. A fiber, incorporated into the intravascular catheter is used for delivering light from an external source such as a superluminescent diode, to the tissue to be diagnosed, and for collecting the retroreflected light. The distal end of the catheter is provided with a mirror, brought into rotation from outside the body by an electrical motor.

A Michelson interferometer is used for analysis of the retroreflected light and for recovering the reflectance profile along the light beam. A movable mirror in the reference arm of the interferometer is moved in a sequence of positions, and the intensity of the interfering light is measured for each position, thus providing a plot of the reflected intensities as a function of depth into the tissue. A dithering of the reference mirror is combined with a phase locked detector to overcome 1/f noise. Rotation of the mirror at the distal end of the catheter allows the measurement of reflectance profiles (plots) for different directions around the vessel and to build a computer generated cross-sectional image of the vessel.

A serious drawback of this system employed for recovering the opto-electronic reflectance profile is that only while the reference mirror is at rest can the signal be recovered at all measuring points. The intensity at the output photodetector as a function of reference mirror position oscillates with a period of $\lambda/2$, as usual in those kinds of interferometric systems, and only the reconstructed envelope curve of the oscillation magnitudes follows the intensity profile of the reflected light. Thus to recover the retroreflected profile along 1 millimeter, it takes at least 2000–3000 points, and at each of these points the mirror should be stopped completely. Even with the fastest translation stage available, it takes at least several minutes to measure just one profile. To build the whole 360° image, it takes another factor of 100, thus making the time of measurement of one cross-section above one hour. In other words, the system suggested cannot work in real time, it is too slow, because it is inherently incapable of working "on-the-fly", when measurement for any given position of the reference mirror can be done while the mirror is moving.

Another drawback is that the described device is an over-the-wire catheter and cannot be used simultaneously with a therapeutic device in the artery during intervention. It should be inserted before intervention, and then exchanged with a therapeutic catheter, thus significantly lengthening catheterization time.

All of the known devices have disadvantages which prevent them from being used in intravascular diagnosis. It would be desirable to have a high resolution guidewire based intravascular imaging device which can be used both for diagnostic imaging and for placement of over the wire catheters, providing diagnostic support and real time guidance for percutaneous transluminal coronary angioplasty and similar interventions.

SUMMARY OF THE INVENTION

The present invention is a device for performing intravascular imaging using low coherence interferometry. The device is particularly useful for providing adequate diagnostic support and real-time guidance during percutaneous transluminal coronary angioplasty (PTCA) and other similar procedures.

The high resolution low coherence interferometer and low profile imaging guidewire of the present invention is capable of imaging intravascular obstructions prior to, during and after therapeutic treatment and provides resolution sufficient to identify the nature of the obstruction, and to assess the outcome of a therapeutic procedure. The interferometer and imaging guidewire of the present invention together can achieve an imaging resolution of 10 microns or less.

The device includes a low coherence light source, and a mechanism for splitting the light into a sampling beam and a reference beam. The reference optical path includes a mechanism for causing ramp-wise modulation of the optical length of the reference optical path. The sampling beam propagates through the sampling optical path. The sampling path leads to a vascular sample and terminates at an inner wall of the vessel.

A mechanism for causing ramp-wise modulation of a length of the reference optical path is provided comprising a spiral optical element mounted for rotation on a shaft, and also includes a mechanism for causing the shaft to rotate. The rotational shaft has an axis substantially parallel to the reference beam as the beam approaches the spiral optical element. Preferably, the spiral optical element comprises a mirror having a spiral reflective surface.

An optical sensing mechanism is provided which includes a collimator for collimating light from the sampling optical path. The optical sensing means includes a mirror mechanism for causing the sampling beam to travel toward a vessel wall. The mirror rotates about an axis located substantially in line with an axis of the sampling optical path just prior to entering the optical sensing segment mechanism.

The interferometer of the present invention includes a mechanism for combining reflections from the reference optical path and the sampling optical path. A polarization mechanism for decomposition of each of said optical outputs in two optical signals is provided, as well as a photodetection means for generating electrical signals from the resulting combined optical signals.

An electronic subtraction mechanism for subtracting two electrical signals corresponding to the same polarizations for reducing excessive noise of the light source is provided.

An envelope detection mechanism is provided for forming an envelope of the amplitudes of the electrical signals from the photodetection mechanism. A mechanism for processing the electrical signals to form an image of the vessel is also provided.

The present invention includes an imaging guidewire including a hollow elongated body with a distal end, a proximal end, and a throughbore extending longitudinally therethrough. The imaging guidewire includes an optical fiber extending through the throughbore and an optical connector mechanism for connecting the optical fiber into the sampling arm of the interferometer. A micro optical collimator is provided and is mounted onto a distal end of the fiber. A hermetic housing mounted proximate the distal end of the elongated body is provided which encloses a mirror mechanism. The mirror mechanism is mounted within the housing and has an ability to rotate about a central axis of the throughbore. The mirror mechanism reflects light emanating from the distal end of the micro collimator and collects light retroreflected from the vessel wall. A micromotor mechanism is provided for causing the mirror to rotate. A connection mechanism is provided for providing electrical connection of the micromotor mechanism to a power source.

The present invention includes a harmonic motion micromotor comprising a stator having an inner surface defining a throughbore. A plurality of electrically conductive electrodes are provided and are electrically isolated from a rotor. The electrodes are positioned substantially parallel to the central cylindrical axis of the throughbore and are spaced apart within a wall of the stator. The micromotor also includes a rotor for positioning in the throughbore. The rotor is formed of a ferromagnetic material. The invention also includes a mechanism for passing electrical current through each adjacent electrode to sequentially form individual magnetic fields about each conductive electrode capable of attracting the rotor and causing the rotor to roll around an inner surface of the stator.

A method of imaging vascular stenosis is described. The method includes introducing a low coherence imaging guidewire having a distal end with a housing proximate the distal end and an angular scanner mounted within a housing into the patient's vascular system. The distal end is positioned slightly past the site to be treated and the housing is positioned adjacent the site. The method includes imaging the site using Doppler interferometric imaging. The method further includes the steps of forming an image of the site and evaluating information presented in the image for developing an interventional strategy.

DETAILED DESCRIPTION

The present invention is a novel device for identifying the geometry and morphology of an intervascular obstruction before, during or after a therapeutic procedure employing over-the-wire catheters such as a PTCA catheter, for example. The device of the present invention employs the use of Doppler interferometry and an imaging guidewire in order to create cross-sectional images of obstructed vessels. The present invention is also a diagnostic method which can provide assistance to the cardiologist in directing treatment of atherosclerosis which employs visualization of the lesions using an imaging guidewire and a Doppler interferometer.

The preferred low coherence interferometer and imaging guidewire of the present invention provide resolution of 10 microns or less, and is particularly useful for providing a visual display of a cross-section of a vessel wall. This visual information is useful for diagnosing the nature of a lesion, and represents a significant advancement in diagnostic tools that are currently available for diagnosing the specific type of atherosclerotic lesions being encountered.

Figure 1:
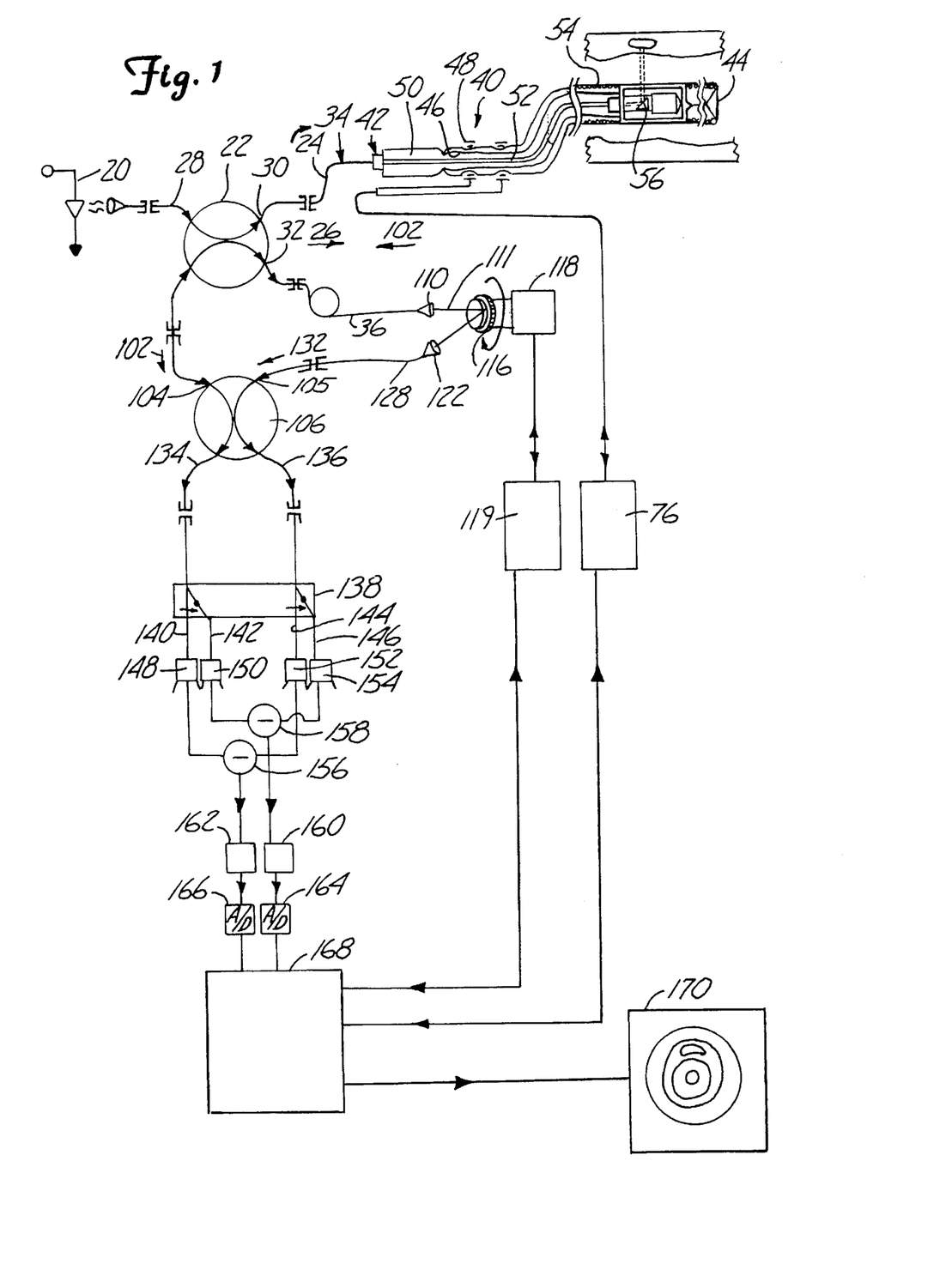
FIG. 1 is a schematic diagram illustrating a preferred Doppler interferometric imaging apparatus and imaging guidewire of the present invention.

The preferred interferometer is shown schematically in FIG. 1. A low coherence light source 20 such as a superluminescent diode or light emitting diode is provided. Preferred operational wavelengths for the light source are 830, 1300 and 1550 nanometers. Most preferably a light source having an operable wavelength of 1550 nanometers is employed, because it is a readily available wavelength of light sources and is standard in the communications industry. In addition, a 1550 nanometer light source is also preferred because it has a low attenuation in biological tissue.

A first directional coupler 22 is provided which splits a beam of light into two separate beams; a sampling beam 24 and a reference beam 26. The light from the light source 20 is coupled to a first input 28 of the first directional coupler 22. The sampling beam 24 exits the first directional coupler 22 from a first output 30. The reference beam 26 exits the first coupler 22 from a second output 32. Both the sampling and reference beams 24 and 26 pass through optical fibers 34 and 36, respectively. The optical fibers 34 and 36 are single mode fibers (SMF).

The present invention includes an imaging guidewire 40 having a proximal end 42 and a distal end 44. The imaging guidewire 40 of the present invention includes a hollow elongated body 46 which has a throughbore 48. Preferably, the hollow elongated body 46 has an outer diameter between about 0.35 millimeters and about 0.46 millimeters, and preferably about 0.35 millimeters. The hollow elongated body 46 has inner diameter of between 0.26 millimeters and 0.31 millimeters, preferably about 0.28 millimeters. The hollow elongated body may be constructed of an extruded stainless steel tube or other construction, and preferably includes a flexible distal end formed from a coated spiral wire. The hollow elongated body must have sufficient bending flexibility and enough torsional strength to be steered through a vascular system. Of particular importance to this invention is the size of the outer diameter of the hollow elongated body 46. The outer diameter is selected to be small enough to function as a guidewire for a therapeutic catheter.

Removably attached to the proximal end 42 of the hollow elongated body 46 is an electro-optical fiber connector 50 which in the preferred embodiment is a single mode fiber connector. An optical fiber 52 is positioned within the throughbore 48 of the hollow elongated body 46. The sampling beam 24 propagates from the first coupler 22, along the optical fiber 34 through the electro-optical fiber connector 50, and through the entire length of the optical fiber 52 to a collimator 54.

Figure 2:
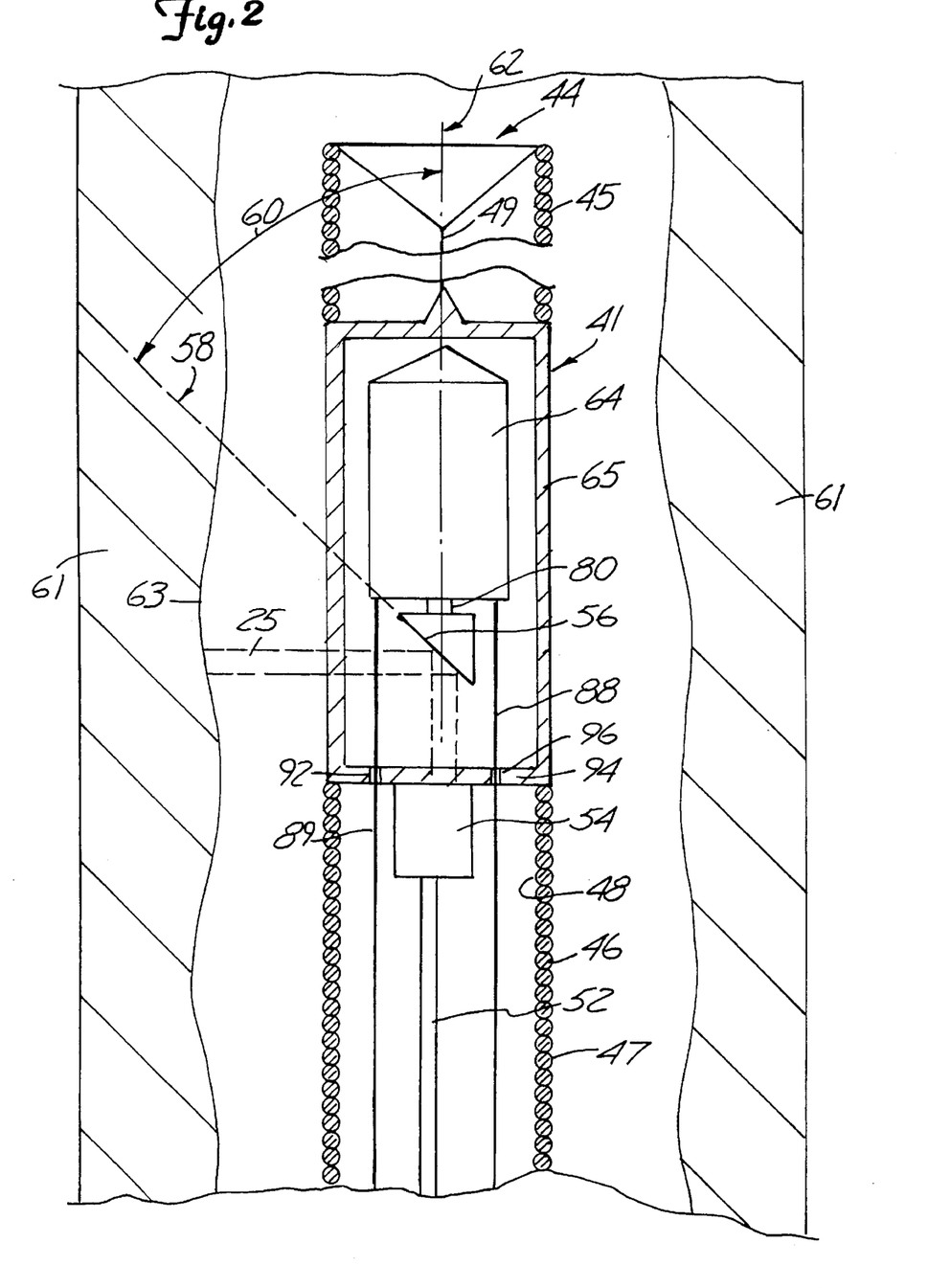
FIG. 2 is a schematic cross-sectional diagram of a distal end of an imaging guidewire of the present invention.

The collimator 54, as best shown schematically in FIG. 2 preferably includes a graded index lens which is formed from graded index fiber. Preferably, the graded index lens is approximately ¼ pitch. The collimator 54 produces a collimated beam having an outer diameter of between 25 and 60 microns. The lens preferably has a focal distance of around 100 to 300 microns. The short focal length is needed to effectively and efficiently collect the light from the different tissue depths. The imaging guidewire 40 of the present invention has a distal end 44. An optical sensing segment 41 is mounted proximate the distal end. What is meant by "proximate" in this context is within a flexible region of the distal end. Typically, the flexible distal end is up to five inches long and is provided to aid in steering the guidewire through a patient's vascular system.

In the preferred embodiment, the flexible region includes first and second spiral-wound wire segments 45 and 47, the first segment 45 wound over a safety wire 49. The second segment 47 preferably does not require a safety wire, due to the presence of optical fiber 52 and wire leads 88 and 89 which are described in more detail below.

The preferred sensing segment 41 includes a housing 65 which is positioned between flexible segments 45 and 47 and which preferably is hermetically sealed and transparent to light in the selected wavelength range. Rotationally mounted in the housing 65 is a mirror 56 for receiving light from the collimator 54.

The collimated beam 25 from collimator 54 is reflected off of the mirror 56 which in the preferred embodiment has a substantially flat surface which is in a plane 58 which is at an angle 60 of about 40 degrees with respect to a central longitudinal axis 62 of the hollow elongated body 46. Although a preferred angle of 40 degrees is used, the invention includes angles that are slightly smaller or larger, such as 30–60 degrees, for example. The angle is selected such that the light reflected from the walls of the housing has an angle greater than the angle of acceptance of the fiber. It is important to avoid capturing strong reflections from the walls of the housing because the reflections can overload the sensitive photodetection means.

During operation, beam 25 in the preferred embodiment rotates about pivotal axis 62, scanning a full 360 degrees around the inner surface of the vessel 63. However, the device of the present invention can be adapted to rotate less than a full 360 degrees during sampling. The collimated beam 25 is reflected off of an inner surface 63 of the vessel 61, and the light is collected by the mirror and focused into the optical fiber 52, by the collimator 54, returning to the first coupler 22.

A preferred mechanism for causing the mirror 56 to rotate about the central elongated hollow body axis 62 is a novel micromotor 64. The micromotor 64 and the mirror 56 are preferably enclosed in a hermetically sealed housing 65 and are mounted such that the motor causes the mirror 56 to rotate about axis 62.

Figure 3:
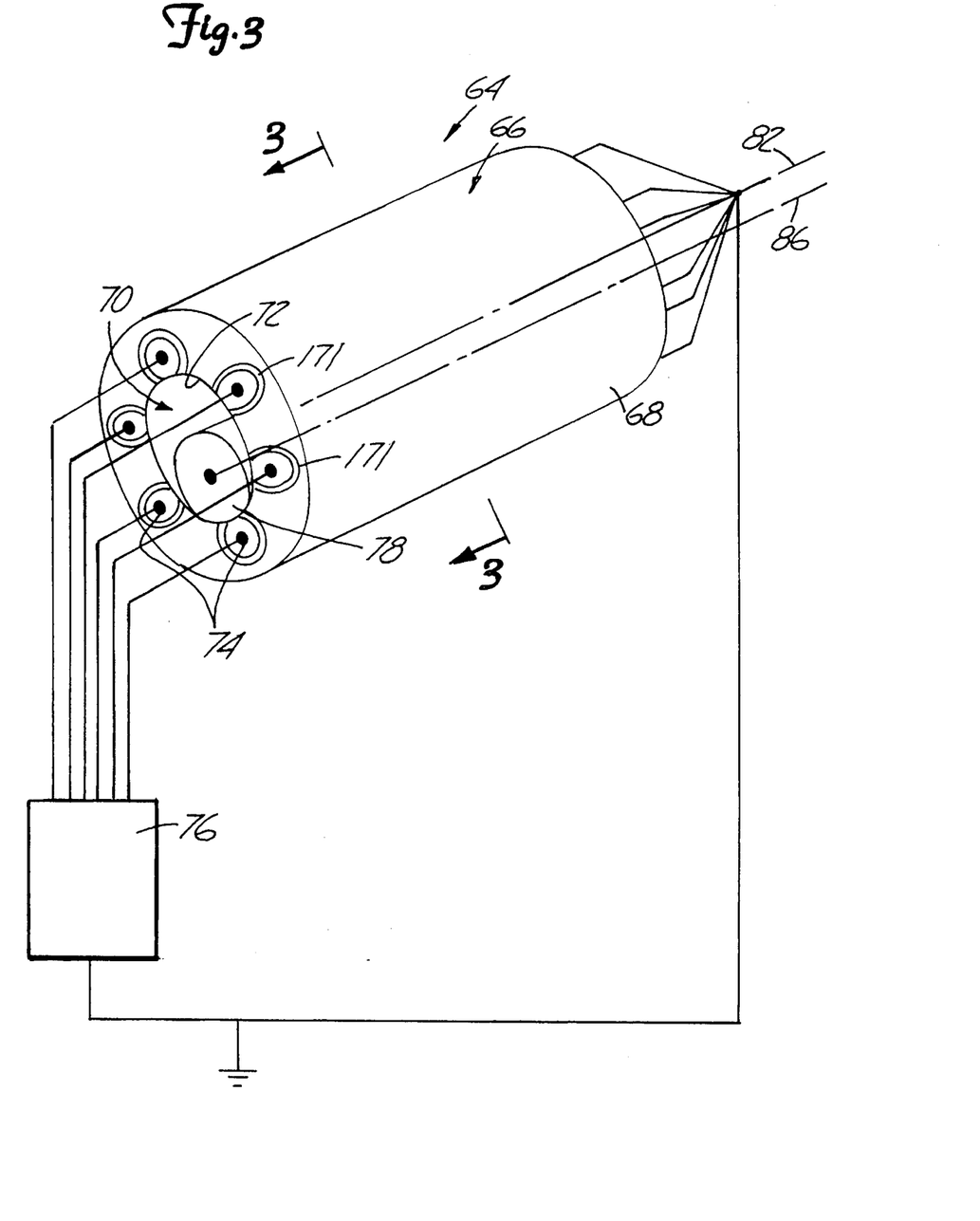
FIG. 3 is a schematic diagram of a magnetostatic micromotor of a preferred embodiment of the present invention.

Referring to FIG. 3, the preferred means for rotating the mirror is described below. The micromotor 64 of the present invention is a harmonic motion micromotor 64. The micromotor 64 includes a stator 66. The stator 66 has an outer surface 68, a substantially cylindrical throughbore 70 and an interior surface 72. Mounted within or preferably integrally formed within a wall of the stator 66 are a plurality of stator electrodes 74 which are in electrical contact with a micromotor controller 76. The controller 76 includes an electrical current generator (not shown) and a switch (not shown) capable of delivering current to each individual stator electrode 74 at a separate point in time, and according to a selected sequence. Preferably, each current is supplied to each adjacent electrode 74 located along a circumference of the throughbore separately, and only to one electrode 74 at a time. Electrodes 74 are surrounded by elongated clamps 171 formed from a soft ferromagnetic material such as nickel or permalloy. Preferably, each clamp 171 extends along an entire length of the stator. Most preferably, the clamps are longer than a length of the ferromagnetic portion of the rotor. Such an arrangement causes the rotor to levitate and to remain longitudinally centered in the stator during operation.

The micromotor of the present invention also includes a rotor 78 which in the preferred embodiment is coupled to a stem 80 of the mirror (shown in FIG. 2). The rotor 78 is preferably has a central portion (not shown) constructed of a soft ferromagnetic material such as nickel or permalloy which is attracted by a magnetic field created by electrical current passing through the electrode 74. The force attracting the rotor to an electrode 74 and the torque exerted on the rotor are significantly enhanced by using clamps 171. The clamps 171 are provided for concentrating the magnetic field surrounding each electrode.

Figure 4:
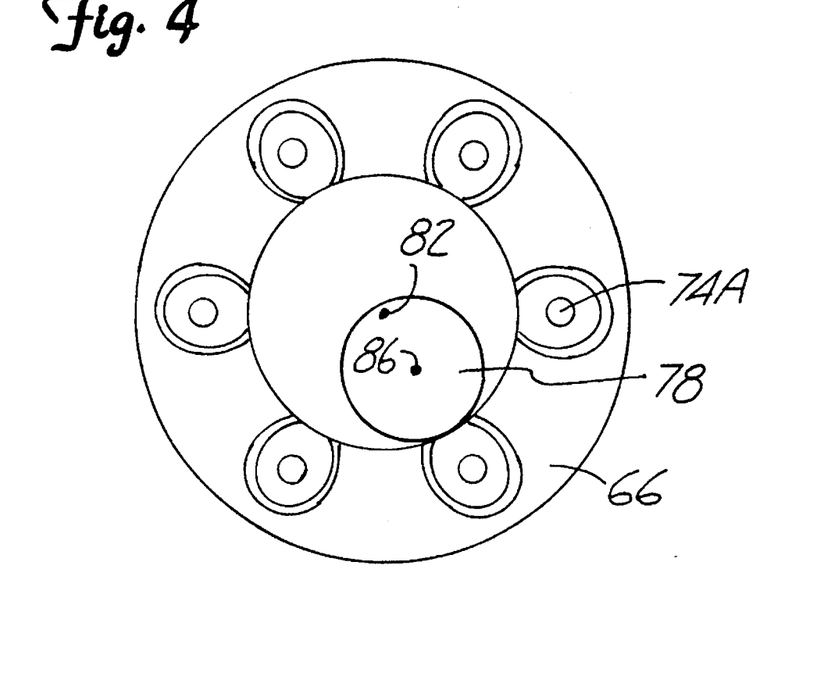
FIG. 4 is a cross-sectional view of a first preferred magnetostatic harmonic motion micromotor, taken along line 3—3 as shown in FIG. 3.
Figure 5:
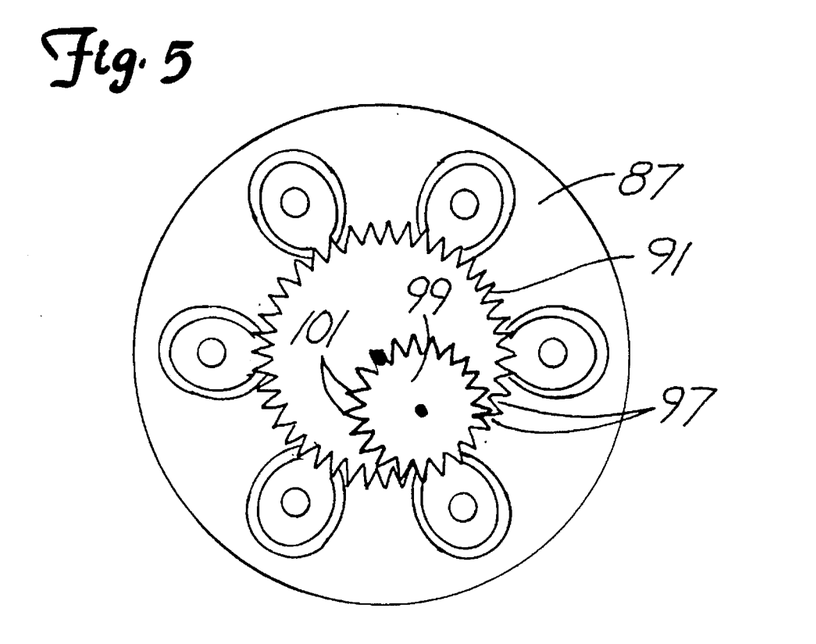
FIG. 5 is a cross-sectional view of a second preferred magnetostatic harmonic motion micromotor of the present invention.

The operation of the micromotor of the present invention can be better understood by referring to FIGS. 4 and 5. FIG. 4 is a cross-sectional view of a first preferred micromotor 64, taken along line 3—3 as shown in FIG. 3. As the switch (not shown) of the micromotor controller 76 (shown in FIG. 3) directs the electrical current in sequence to an individual electrode, for example 74A, the rotor 78 is attracted to the electrode by a magnetic field created by the current passing through the electrode. Preferably, current only passes through one electrode 74 at a time. Rotor 78 therefore rolls step-wise within the stator 66. It is to be understood that a central axis 82 (into the paper) of the stator 66 is parallel to a central axis 86 (into the paper) of the rotor 78 as the micromotor 64 operates. Although a distance between central axis 82 and central axis 86 is greatly exaggerated in FIG. 4 for clarity, it is to be understood that the distances between axis in the preferred micromotor 64 are quite small, for instance, approximately 0.001 millimeters while the micromotor 64 is in motion. Because the diameters of the rotor and stator throughbore 70 are different, the motion of the rotor 78 is harmonic as well as rotational with respect to the stator. For example, for a stator throughbore having an inner diameter of 101 microns and a rotor outer diameter of 100 microns, the rotor will rotate once per every one hundred harmonic motions. Preferably, the micromotor 64 causes the mirror 56 (shown in FIG. 2) to rotate in a single direction during operation.

The outer diameter of the rotor 78 and the inner diameter of the stator 66, as well as the switching speed of the controller 76 and the current delivered to the electrodes 74 all determine the rotational speed of the mirror 56. Preferably, the micromotor 64 causes the mirror to rotate at between 5 and 500 Hz.

Referring now to FIG. 5, in a second preferred embodiment, the stator 87 has an inner surface 91 having a plurality of teeth 97 defining a gear. The rotor 99 has an outer surface with teeth 101 which cooperate with teeth 97. The teeth 97 and 101 cause the angular position of the mirror (not shown) to be more precisely defined.

Referring back to FIG. 2, the micromotor 64 includes wire leads 88 and 89 which extend through apertures 90 and 92 in the base 94 of sealed housing 65 and through the throughbore 48 of the hollow elongated body 46 to the proximal end 42. Although only two wire leads 88 and 89 are shown, it is to be understood that the number of leads will vary, depending upon the location of the switch that controls the current to each individual electrode 74. If the switch is provided in the form of a microswitch located on the stator 66, then it would be possible to use only two leads; one to ground and one supplying current to the microswitch (not shown). If the switch is located within the controller 76 for example, then seven leads would be needed; one for ground, and the remaining leads to supply current to each of the individual electrodes 74.

Figure 6:
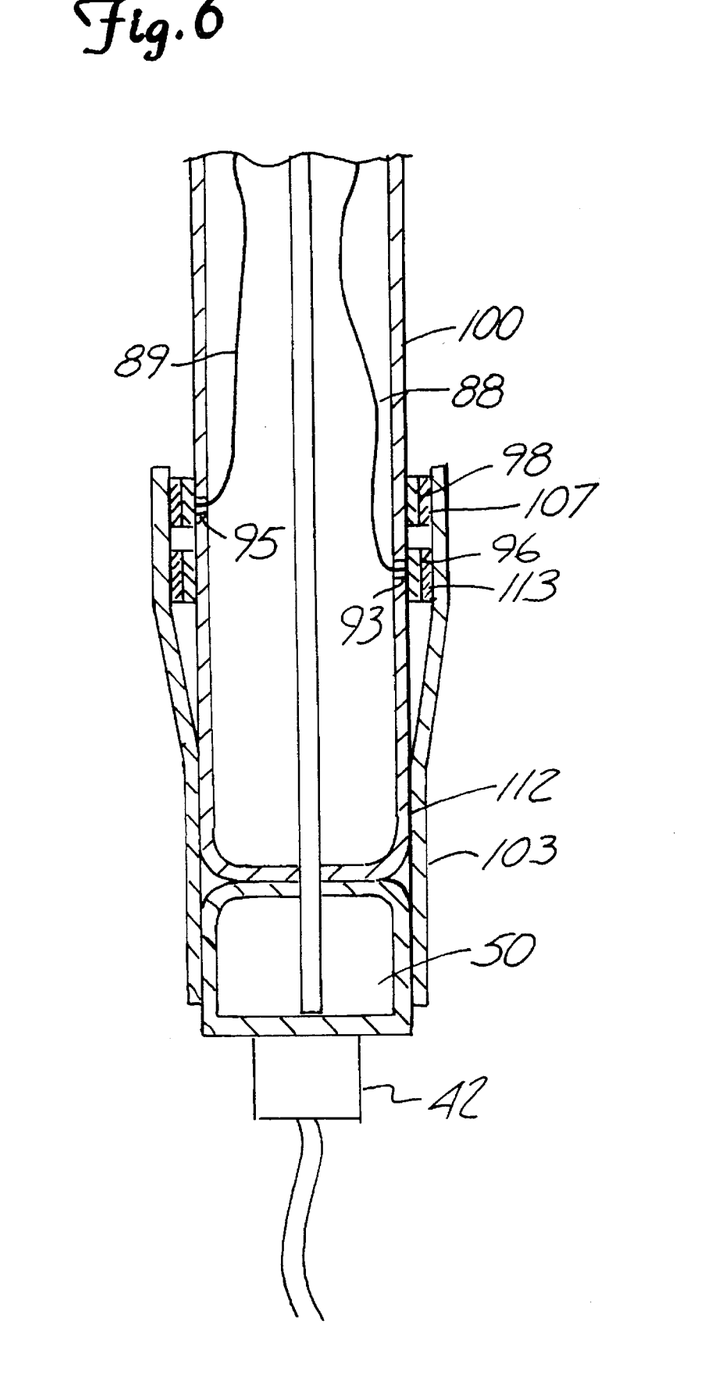
FIG. 6 is a schematic cross-sectional view of the proximal end of the preferred imaging guidewire of the present invention.

Referring now to FIG. 6, a cross-sectional schematic view of the proximal end 42 of the imaging guidewire 40 of the present invention is shown. The wire leads 88 and 89 extend along substantially the entire length of the hollow elongated body 46. Proximate the proximal end 42 of the hollow elongated body 46, a pair of apertures 93 and 95 extend through the wall of the hollow elongated body and the leads 88 and 89 extend therethrough to a point on an outer surface of the hollow elongated body. Electrically conductive bands 96 and 98 extend around an outer surface 100 of the hollow elongated body and are provided to electrically connect the micromotor controller 76 (shown in FIG. 2) to the micromotor 64. An electro-optical fiber connector 50 is also provided for connecting the distal end 42 of the imaging guidewire 40 to a micromotor controller 76. A coupling 103 which is preferably part of the electro-optical connector 50 is provided for securing the connector 50 to a distal end 112 of the hollow elongated body. The coupling 103 includes electrodes 107, 113 on an interior surface which come into electrical contact with bands 96 and 98 when the coupling 103 is in an operable position on the proximal end of the guidewire.

Referring back to FIG. 2, in operation, the mirror 56 reflects light delivered to it by the collimator 54. The light passes through the housing 65 which is transparent, and then preferably passes through a fluid such as saline solution which is transparent to light at the wavelengths being delivered. The saline solution is preferably injected to displace the blood in the vessel prior to imaging to reduce attenuation of light in the vessel.

Referring back to FIG. 1, the light reflected back from the tissue is gathered by the mirror 56, is sent to the collimator 54 and is focused back into the optical fiber 52 where the light then passes through optical fiber 34, and reaches the first directional coupler 22. The light beam which returns to the first directional coupler 22 is split into two beams. A first beam returns to the light source 20 and vanishes. The second beam 102 enters into a first input 104 of a second directional single mode coupler 106.

As mentioned above, the first directional coupler 22 splits radiation from the light source 20 into a sampling beam and a reference beam. The optical path of the sampling beam has been described above. The following is a description of the path of the reference beam.

Figure 7:
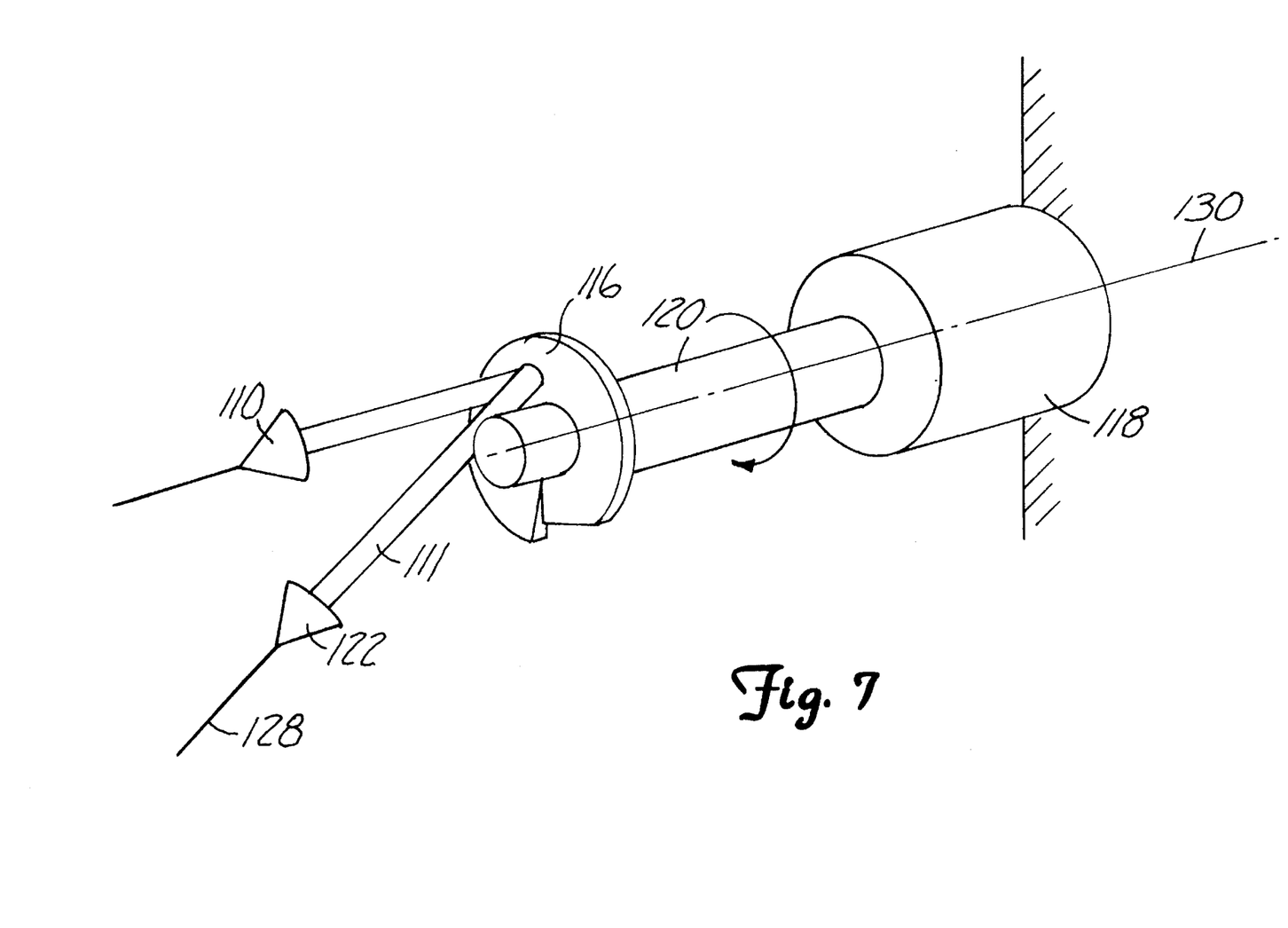
FIG. 7 is a schematic diagram of the spiral mirror and electromotor of a preferred embodiment of the device of the present invention.

From the first directional coupler 22, a beam of light 26 passes through optical fiber 36 to a beam collimator 110 which collimates the beam 111 and directs the beam 111 onto a spiral mirror 116, which is shown in detail in FIG. 7.

An electric motor 118 having a rotational shaft 120 is provided. The rotational shaft 120 is fixedly coupled to the mirror 116 in the preferred embodiment. The motor 118 is controlled by a controller 119 (shown schematically in FIG. 1). The controller 119 generates current, supplies the electrical current to the motor 118 and tracks the angular position of the spiral mirror 116. The controller 119 also controls the rotational speed of the motor 118.

The light reflected off of a surface of the spiral mirror 116 during rotation impinges on a second collimator 122 which refocuses the light into an optical fiber 128, shown in FIG. 1. The reference beam 111 is sent into a second input 105 of the second coupler 106.

As the mirror 116 rotates about a central axis 130 (shown in FIG. 7), the point on a surface of the spiral mirror 116 where light is reflected shifts back and forth in a direction parallel to central axis 130, providing ramp-wise modulation of the length of the reference arm of the device of the present invention. Preferably, the rotational rate of the spiral mirror is between about 100 and about 1000 hertz, most preferably about 400 hertz.

Because the motion of the spiral mirror 116 does not require translational movement of the mass of the mirror in the reference arm, the spiral mirror eliminates many of the speed and power limitations of the low coherence interferometers known in the art. The device of the present invention causes the length of the reference arm to be modulated in a manner which results in very fast scanning speeds, which were unknown before the device of the present invention. High scan speeds are necessary for intravascular real-time imaging. The scanning time span is much shorter than the time span of biological movements and therefore real-time scanning can be achieved.

The operation of the second coupler 106 will now be described. The reference beam 132 passing through the optical fiber 128 is inputted into the second coupler 106. The retroreflected radiation 102 returning from the tissue and passing through the first coupler 22 is inputted into the second coupler 106 and is combined with the reference beam 132.

Directional coupler 106 combines the two beams 132 and 102 and causes them to interfere. The outputs from the second directional coupler 106 are two optical beams 134 and 136. Both beams preferably travel through an optical fiber. In each of the output beams 134 and 136, a different interferometric output is present. The oscillation of intensity of the two output signals are opposite in phase.

The interferometric patterns in the two output beams 134 and 136 in part depend upon the light polarization of the beams. For this reason, a polarization beam splitter 138 is provided to split the polarizations in the two output beams 134 and 136, producing four distinct output beams 140, 142, 144 and 146. The four output beams are inputted into four photodetectors 148, 150, 152 and 154. The photodetectors convert the optical signals to electrical RF Signals.

The output signals from photodetectors 148 and 152 are combined in a subtraction scheme 156. Similarly, the output signals from photodetectors 150 and 154 are combined in a subtraction scheme 158. The subtraction schemes 156 and 158 generate optical anticorrelation signals which double the amplitude of the maxima of the signals, and subtract the excessive intensity noise. The resulting signals are inputted into two envelope detectors 160 and 162.

The envelope detectors 160 and 162 function to filter out the carrier frequency equal to the Doppler shift and forman amplitude envelope of the RF signal. A signal representing the dependence of the retroreflected light amplitude as a function of time is obtained. The output from the envelope detectors are related to two different polarizations of light. This output is digitized in analog to digital transducers 164, 166. The output signals from the transducers 164 and 166 are inputted into a computer means 168 which also receives signals from the motor controller 119 and the micromotor controller 76. The computer uses the information from the controller 119 which identifies the location of the mirror to calculate the length of the reference arm. This information, along with the outputs from transducers 164 and 166 are used to create an image on a visual display such as a video screen 170, for example. The video screen 170 is connected to the computer means 168 and is capable of showing a real-time, cross-sectional view of the blood vessel.

In order for the device of the present invention to be capable of producing signals which can be processed by a computer to generate a visual display of a cross-section of tissue being scanned, it is necessary to select a length of the reference arm approximately equal to the length of the optical path of the sampling arm. The distance of the optical path of the reference arm is measured between couplers 22 and 106. The distance of the optical path of the sampling arm is measured between coupler 22, to the tissue to be sampled, back to coupler 22 and through to coupler 106.

The rotating mirror 116 is important for two reasons. First, the optical length of the reference beam is continuously ramp-wise modulated, causing a Doppler frequency shift in the reference beam. The shift is described by the following formula:

$$\Delta f = 2\, v/\lambda \tag{1}$$

where v is the speed that the mirror surface is moving in the direction of the reference beam from the collimator 110, and $\lambda$ is the average wavelength of the radiation.

The range of acceptable rotational rates is estimated to be between about 5 and about 500 hertz. The acceptable range of wavelengths as mentioned above ranges between about 830 and about 1550 nanometers. Using the device of the present invention and using the selected velocity and wavelengths, a Doppler shift equal to between two hundred kilohertz and two megahertz can be obtained.

The RF signal which is generated by the device of the present invention has a carrier frequency which is equal to the Doppler shift. The outputs from the envelope detectors each have an amplitude which is proportional to the amplitude of the retroreflected light from the tissue. A balanced scheme allows subtraction of excessive noise from the light source.

As stated above, the amplitude of the RF signal from the envelope detectors 160, 162 is proportional to the amplitude of the reflected light. As a function of the reference optical length, the envelope of the RF signal represents the profile of optical reflection verses depth into the tissue. The signal frequency is defined by the Doppler shift resulting from the optical length modulation produced by the rotating spiral mirror 56.

The signal from envelope detectors 160, 162, and information on the length of the reference arm as a function of time are inputted into the system computer 168. The computer recovers a profile of the reflection signal as a function of tissue depth. This information, when combined with information on the angular position of the mirror 56, enables the computer to generate a two dimensional image of the blood vessel which is displayed on video screen 170 and which is used for diagnosis.

The Doppler interferometer and imaging guidewire of the present invention together form images based on information gathered during scanning in as little as a tenth of a second, which is faster than the time between even the fastest heart beat of a patient. Scanning rates of such short duration obtained by known low coherence interferometers were not possible before the present invention.

The method of the present invention employs the use of a device such as the one described above to perform real-time imaging of blood vessels for the diagnosis of atherosclerosis and for the selection of a therapeutic treatment.

Figure 8A:
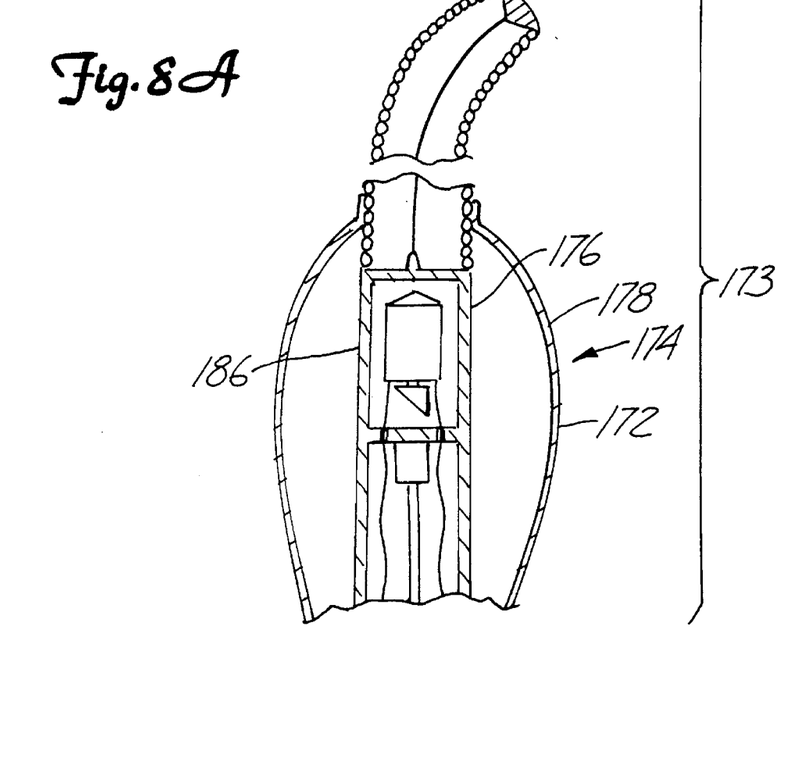
FIG. 8 is a schematic diagram of a proximal and distal end of a second preferred imaging guidewire of the present invention.
Figure 8B:
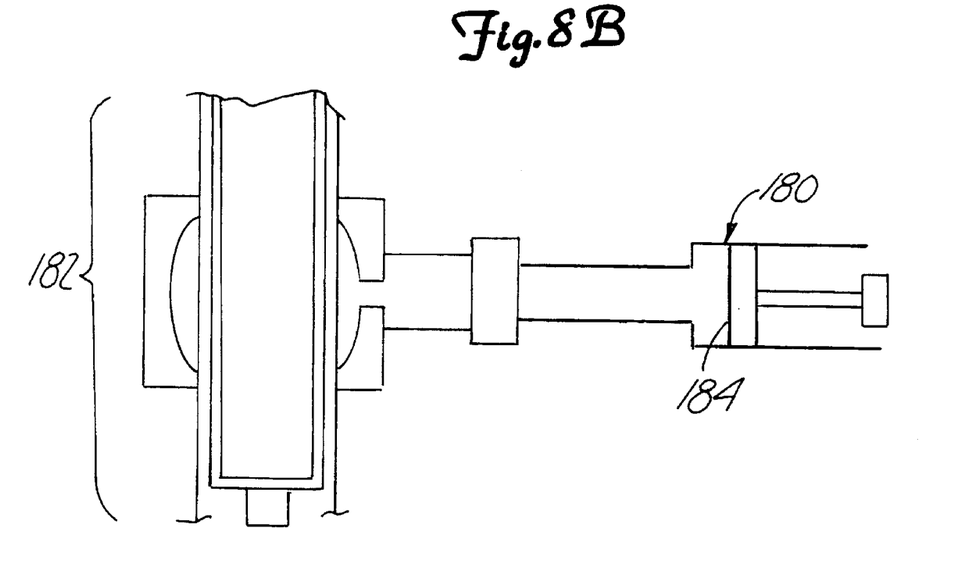

A second embodiment of an imaging guidewire of the present invention is shown in FIG. 8. FIG. 8 shows the distal end 173 of an imaging guidewire 174 of the present invention, which is substantially identical to the imaging guidewire illustrated in FIG. 2 except that the distal end 173 is equipped with a balloon 172 surrounding the housing 176 of the guidewire near the distal end. Preferably, a low pressure flexible balloon is used. The size of the balloon is preferably small enough when deflated to permit a therapeutic over the wire catheter to pass over its outer surface.

A syringe 180 located at proximate end 182 of the imaging guidewire, fluidly connected to the balloon 172 by conventional means is provided to inject an optically transparent liquid into the balloon 172 until the balloon contacts the lesion and displaces all of the localized blood. The balloon advantageously centers the sensing segment 186 in the vessel. Use of the balloon also eliminates the hindering effects of movement of the biological tissue on images. Superior resolution of about 10 microns can be achieved with the low coherence system and imaging guidewire of the present invention. Immobilization of the sensing segment also increases the signal to noise ratio because longer averaging times can be used. The balloon 172 can be filled with a liquid 184. When an imaging guidewire of this type is used, the need to displace blood with a saline injection into the blood vessel is eliminated.

The use of an imaging guidewire employing a balloon has the added advantage in that physical information about the vessel and lesion can be ascertained from the behavior of the vessel and lesion in response to pressure applied from the fluid in the balloon. For example, the vessel can be expanded and the elasticity of the vessel wall visualized. If the vessel wall is relatively elastic, then calcification can be ruled out. The degree of "organization" of thrombus can also be determined by the degree of displacement of the obstruction in response to pressure exerted. Providing a second means for identifying disease in a blood vessel in addition to providing visualization of the vessel greatly increases the probability of successfully identifying the composition of the obstruction and the appropriate therapeutic intervention.

The method of the present invention includes the step of introducing a low coherence imaging guidewire into the vascular system of a patient. An imaging guidewire having a diameter suitable for use as a guidewire for an over-the-wire therapeutic catheter is preferred. The imaging guidewire having a distal end with a housing and an angular scanner mounted therein is inserted such that the distal end just passes the site to be imaged, and the housing is located adjacent to the obstruction. The blood in the vessel near the site to be imaged is preferably displaced with a more optically transparent material for an improved signal to noise ratio of the image. The blood near the lesion is preferably displaced with an optically transparent liquid such as saline, or the blood is displaced with an optically transparent balloon surrounding the housing located near the end of the imaging guidewire.

Next, the site is imaged using the Doppler interferometric device which includes a means for ramp-wise modulation of the reference arm described in detail above. A computer preferably receives the information and converts the information into a video output which includes a visual display of a cross-section of the vessel. The method of the present invention includes forming a cross-sectional image of a site and evaluating information presented in the image for developing an interventional strategy. Imaging can take place before, during and after completion of a procedure.

Although the present invention has been described with reference to the preferred embodiments, workers skilled in the art will recognize that changes may be made in form and detail without departing from the spirit and scope of the invention.

What is claimed is:

1. An interferometer for performing real time intravascular imaging, comprising:

a low coherence light source;

means for splitting the light source into a sampling beam and reference beam;

a reference optical path for receiving the reference beam, wherein the reference optical path leads to a means for causing ramp-wise modulation of a length of the reference optical path length;

a sampling optical path for receiving the sampling beam, the sampling optical path leading to a vascular sample and terminating at an inner wall of a vessel;

means for ramp-wise modulation of a length of the reference optical path length comprising a spiral optical element with a spiral receiving surface, a rotational shaft, the spiral receiving surface mounted on the rotational shaft, the shaft having an axis positioned substantially parallel with axis of the reference beam as the reference beam approaches the spiral receiving surface, and means for causing the shaft to rotate;

means for combining reflections from the reference optical path and sampling optical path;

a polarization means for decomposition of each of said optical outputs into two optical signals with orthogonal polarizations;

photodetection means for generating electrical signals from the resulting combined optical signals;

electronic substation means for subtracting two electrical signals corresponding to the same polarizations for reducing excessive noise of the light source;

envelope detecting means for forming an envelope of an amplitude of the electrical signals from the photodetection means; and means for processing said electrical signals to form a cross-sectional image of the vessel.

2. The interferometer of claim 1, wherein the spiral optical element comprises a rotating spiral reflective surface for receiving a reference beam.

3. The interferometer of claim 1, wherein the spiral optical element comprises a rotating optically transparent member having a spiral surface for receiving a reference beam.

4. The interferometer of claim 1 and further comprising an imaging guidewire comprising:

an elongated cylindrical body having a proximal and distal end and a throughbore extending therethrough;

an optical fiber extending through the throughbore;

an optical connection means for optically connecting the optical fiber to the light source.

5. The interferometer of claim 1 wherein the means for causing the shaft to rotate further comprises an electromotor means for causing the shaft to rotate at a speed between about 5 and about 500 Hc.

6. The interferometer of claim 1 wherein the means for combining reflections from the reference optical path and sampling optical path further comprises an electromotor having a shaft, wherein a mirror is mounted onto the shaft, and further comprising a control means for:

providing current to the electromotor;

tracking the angular position of the mirror;

controlling a rotational speed of the shaft; and sending signals to the means for processing the electrical signals.

7. A device for real time intravascular imaging, comprising:

an imaging guidewire having an elongated hollow body with a distal and proximal end and a throughbore extending therethrough, an optical fiber positioned in the throughbore; a micro optical collimator positioned at distal end of the fiber; a housing proximate the distal end of the guidewire proximate said collimator; a mirror positioned in the housing and capable of rotating about a central axis of the throughbore; micromotor means for rotating the mirror; and connection means for providing electrical connection of the micromotor means to a power source;

a fiber optic interferometer comprising:

a low coherence light source;

a beam splitting means for splitting light into a reference and a sampling beam;

a reference arm for receiving the reference beam;

means for causing ramp-wise modulation of a length of the reference arm comprising a spiral optical element with a spiral receiving surface, a rotational shaft, the spiral receiving surface mounted on the rotational shaft, the shaft having an axis positioned substantially parallel with an axis of the reference beam as the reference beam approaches the spiral receiving surface, and means for causing the shaft to rotate;

a sampling arm extending through the guidewire, terminating at a vessel wall; means for combining optical signals from the reference arm and the sampling arm and for generating two optical outputs;

a polarization means for decomposition of each of said optical outputs into two optical signals with orthogonal polarizations;

photodetection means for converting the optical signals to electrical RF signals; electronic subtraction means for subtracting two electrical signals corresponding to the same polarizations for reducing excessive noise of the light source;

envelope detection means for restoration of the amplitude envelope of the RF signals;

means for converting the outputs from the envelope detection means into digital signals;

computer means for receiving the digital signals and processing the information to reconstruct cross-sectional images of a vessel; and display means for displaying cross-sectional images of the vessel.

8. An imaging guidewire, comprising:

an elongated hollow body with a distal end, a proximal end and a throughbore extending longitudinally therethrough;

an optical fiber extending through the throughbore;

a micro optical collimator positioned at a distal end of the optical fiber;

an optical connector means for connecting the proximal end to a low coherence interferometer;

a hermetic housing mounted proximate said distal end of the hollow body proximate the collimator;

a mirror mounted within said housing for reflecting light emanating from said collimator in a generally transverse direction and to the vessel walls, said mirror mounted for rotation about an axis substantially in line with a central throughbore axis;

a micromotor means positioned proximate the distal end for rotating the mirror; and connection means for providing electrical connection of the micromotor means to a power source.

9. The imaging guidewire of claim 8, wherein the mirror comprises a reflective surface located in a plane that intersections a longitudinal axis of a light beam exiting the micro optical collimator, wherein an angle formed between the longitudinal axis and the plane is between about 35 and about 55 degrees.

10. The imaging guidewire of claim 8, wherein the elongated hollow body has an outer surface, and the connection means comprising at least on electrically conductive contact positioned on the outer surface of the elongated body.

11. The imaging guidewire of claim 8, wherein the optical fiber is a single mode fiber.

12. The imaging guidewire of claim 8 and further comprising a balloon located proximate the distal end and enclosing the housing, and a syringe fluidly connected to the balloon.

* * * * *

UNITED STATES PATENT AND TRADEMARK OFFICE
CERTIFICATE OF CORRECTION

PATENT NO. : 5,582,171
DATED : December 10, 1996
INVENTOR(S) : Victor Chornenky and Peter Pettig It is certified that error appears in the above-indentified patent and that said Letters Patent is hereby corrected as shown below:

Col. 14, Line 36, after the word "electronic", delete the word "substation" and insert the word --subtraction--

Signed and Sealed this

Tenth Day of June, 1997

Attest:

BRUCE LEHMAN

Attesting Officer   Commissioner of Patents and Trademarks